United States Patent [19]

Surber

[11] Patent Number: 4,709,103

[45] Date of Patent: Nov. 24, 1987

[54] PROCESS FOR THE PREPARATION OF ALKALI METAL ALCOHOLATES

[75] Inventor: Werner Surber, Oberwil, Switzerland

[73] Assignee: CIBA-GEIGY Corporation, Ardsley, N.Y.

[21] Appl. No.: 829,335

[22] Filed: Feb. 14, 1986

[30] Foreign Application Priority Data

Feb. 20, 1985 [CH] Switzerland ............................ 791/85

[51] Int. Cl.$^4$ ....................... C07C 29/70; C07C 31/30
[52] U.S. Cl. ..................................... 568/851; 548/453
[58] Field of Search ......................................... 568/851

[56] References Cited

U.S. PATENT DOCUMENTS

| | | | |
|---|---|---|---|
| 2,000,329 | 5/1935 | Heisel et al. | 568/851 |
| 2,732,284 | 1/1956 | Sakowski | 568/851 |
| 3,971,833 | 7/1976 | Lenz et al. | 568/851 |
| 4,150,244 | 4/1979 | Knorre et al. | 568/851 |
| 4,579,949 | 4/1986 | Rochat et al. | 546/167 |

FOREIGN PATENT DOCUMENTS 2612642 9/1977 Fed. Rep. of Germany ...... 568/851

OTHER PUBLICATIONS

Du Pont, "Sodium Products Bulletin".

Primary Examiner—J. E. Evans
Attorney, Agent, or Firm—Harry Falber

[57] ABSTRACT

A process for the preparation of alkali metal tertiary alcoholates by reacting an alkali metal with a tertiary alcohol, which process comprises adding the hot alcohol, with stirring, to the melted alkali metal. Said process has the advantage that no inert solvents are required.

4 Claims, No Drawings

PROCESS FOR THE PREPARATION OF ALKALI METAL ALCOHOLATES

The alkali metal alcoholates of tertiary alcohols have lately found growing interest as catalysts and conditioners since, on account of their low acidity, the corresponding sterically substantially hindered alcohols are particularly effective proton acceptors and usually do not undergo secondary reaction. Alkali metal tertiary alcoholates are important in particular for the preparation of diketopyrrolopyrrole pigments as described e.g. in European published application 94 911.

So far the preparation of alkali metal tertiary alcoholates on an industrial scale has been carried out in an inert solvent such as cyclohexane (q.v. e.g. German Offenlegungsschrift 2 612 642). However, this has the disadvantage that the solvent has to be separated from the alcohol forming during the reaction. Inert solvents are also employed in the processes described in German Auslegeschrift 2 333 634 and British patent specification 746 400 for the preparation of alkali metal alcoholates.

Accordingly, the present invention relates to a process for the preparation of alkali metal tertiary alcoholates, by which process the hot alcohol is added, with stirring, to the melted alkali metal without employing a solvent.

Suitable alkali metals are for example lithium or potassium or, preferably, sodium. It is convenient to melt down the alkali metal under nitrogen.

Preferred tertiary alcohols are those containing 5 to 22 carbon atoms, e.g. 3,7-dimethyl-1,6-octadien-3-ol (linalool), 3,7,11-trimethyl-3,6,10-dodecatrien-3-ol, 3,7,11,15-tetramethyl-1-hexadecen-3-ol, tetrahydrolinalool or, most preferably, tert-amyl alcohol.

It is convenient to use up to 5 moles, preferably 3 to 4 moles, of the alcohol per 1 gram equivalent of the metal.

The alcohol is added to the melted alkali metal gradually and with very vigorous stirring. After the alcohol has been added, the mixture is heated under reflux until all the alkali metal has dissolved. The resultant alcoholic solution can be used direct for syntheses, in particular for the preparation of diketopyrrolopyrroles.

EXAMPLE 1

10.4 kg of sodium bars are placed in a dry 630 liter agitator vessel which has been flushed with nitrogen. The sodium is melted by increasing the jacket temperature to 100°–105° C.

150 kg of tert-amyl alcohol are sucked into a dry 250 liter agitator vessel equipped with anchor agitator and reflux condenser, which vessel has been flushed with nitrogen. The amyl alcohol is heated to boiling point. With stirring and under dry nitrogen, the boiling hot amyl alcohol is slowly added under pressure to the melted sodium. With very vigorous stirring and heating with jacket steam, the mixture is boiled at 102°–114° C. for 4 hours until no more hydrogen is formed, i.e. until all the sodium has dissolved. A clear, colourless to yellowish solution of tert-amyl alcoholate is obtained which can be used direct for synthesis.

EXAMPLE 2

Over 145 minutes, 7.22 kg of benzonitrile followed by an anhydrous as possible solution of 7.31 kg of dimethyl succinate in 5.0 liters of tert-amyl alcohol are added with a metering pump at 98° C. to 48.2 liters of the solution obtained according to Example 1, which solution contains 17.3 kg of sodium tert-amylate. The temperature is held constant at 98°–99° C. The resultant methanol distills. When the addition is complete, the reaction mixture is held for a further 2 hours at 99° C. The mixture is subsequently cooled to 65° C., slowly diluted with 100 liters of methanol, slowly neutralised with 10.8 liters of glacial acetic acid and then briefly boiled at reflux temperature. The resultant pigment suspension is filtered at about 50° C. The filter cake is suspended in 300 liters of methanol, and the pigment is isolated by filtration. Finally, the pigment is washed with methanol and water until the washings run colourless and is dried in vacuo at 80° C., affording 9.04 kg (corresponding to 62.8% of theory, based on dimethyl succinate) of pure pigment of the formula

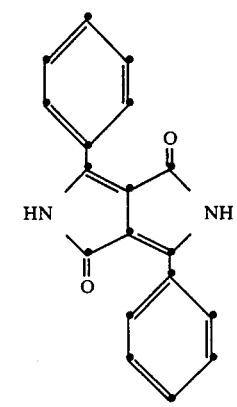

which colours PVC red when incorporated in 0.2% concentration.

EXAMPLE 3

In a dry 750 ml sulfonating flask equipped with blade agitator and reflux condenser, which flask has been flushed with nitrogen, 10.4 g of sodium are melted by heating the oil bath of the reaction flask to 120° C. With stirring, 260 g of 3,7-dimethyl-1,6-octadien-3-ol (linalool) of a temperature of 100° C. are then added through a drip funnel to the melted sodium over 30 minutes. The temperature of the reaction mixture is finally increased to 115°–120° C. After about 90 minutes, the evolution of hydrogen ceases and all the sodium has dissolved. A yellow solution is formed.

EXAMPLE 4

370.7 g of 3,7,11-trimethyl-3,6,10-dodecatrien-3-ol can be employed in place of 260 g of linalool. The procedure is the same as that described in Example 3 except that the reaction lasts about 5 hours until the sodium has dissolved completely. A pale brown solution is formed.

EXAMPLE 5

With stirring and at an oil bath temperature of 125° C., 500 g of 3,7,11,15-tetramethyl-1-hexadecen-3-ol of a temperature of 100° C. are added over 15 minutes to 10.4 g of sodium which have been melted at 108°–109° C. After stirring the reaction mixture for 5 hours at 109°–130° C., the evolution of $H_2$ (i.e. the reaction) is complete. A yellow solution is formed.

EXAMPLE 6

At an oil bath temperature of 125° C., 264 g of tetrahydrolinalool of a temperature of 100° C. are added over 30 minutes to 10.4 g of melted sodium. The mixture is stirred for about 8 hours at 120° C. until all the sodium has dissolved and the evolution of hydrogen ceases. The sodium salt of the tertiary alcohol is yellow.

What is claimed is:

1. A process for the preparation of an alkali metal $C_5$–$C_{22}$ tertiary alcoholate by reacting an alkali metal with a $C_5$–$C_{22}$ tertiary alcohol, which process comprises adding the hot alcohol, with stirring, to the melted alkali metal, the reaction taking place in the absence of any inert solvent.

2. A process according to claim 1, wherein the alkali metal is sodium.

3. A process according to claim 1, wherein the alcohol is tert-amyl alcohol.

4. A process according to claim 1, which comprises the use of up to 5 moles of the alcohol per 1 gram equivalent of the metal.

* * * * *